United States Patent
Addison

(10) Patent No.: US 11,623,044 B2
(45) Date of Patent: Apr. 11, 2023

(54) FALSE ALARM CONTROL AND DRUG TITRATION CONTROL USING NON-CONTACT PATIENT MONITORING

(71) Applicant: Covidien LP, Mansfield, MA (US)

(72) Inventor: Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 523 days.

(21) Appl. No.: 16/805,527

(22) Filed: Feb. 28, 2020

(65) Prior Publication Data
US 2021/0268184 A1    Sep. 2, 2021

(51) Int. Cl.
*A61M 5/172*    (2006.01)
*G06T 7/00*     (2017.01)

(52) U.S. Cl.
CPC ......... *A61M 5/1723* (2013.01); *G06T 7/0016* (2013.01); *A61M 2205/3306* (2013.01); *A61M 2205/50* (2013.01); *A61M 2205/582* (2013.01); *A61M 2230/42* (2013.01); *G06T 2207/10016* (2013.01); *G06T 2207/10028* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 7,179,229 B1 * | 2/2007 | Koh | A61N 1/36114 600/483 |
| 2006/0241510 A1 | 10/2006 | Halperin et al. | |
| 2006/0241708 A1 * | 10/2006 | Boute | A61B 5/4818 607/18 |
| 2014/0275832 A1 * | 9/2014 | Muehlsteff | A61B 5/6889 600/301 |
| 2015/0182131 A1 | 7/2015 | Mahfouz et al. | |
| 2018/0153477 A1 | 6/2018 | Nagale et al. | |
| 2018/0184970 A1 | 7/2018 | Ye et al. | |

OTHER PUBLICATIONS

Zhao, J., Gonzalez, F., & Mu, D. (2011). Apnea of prematurity: from cause to treatment. European Journal of Pediatrics, 179(9), 1097-1105.
International Search Report and Written Opinion issued in PCT Application No. PCT/US2021/019792, dated May 25, 2021, 14 pages.

* cited by examiner

*Primary Examiner* — Manuel A Mendez
(74) *Attorney, Agent, or Firm* — Holzer Patel Drennan

(57) ABSTRACT

Implementations illustrated herein discloses a method of controlling drug titration to a patient, the method including receiving, using a processor, a sequence of depth images, each depth image including depth information for at least a portion of the patient, determining, using the processor, a sequence of physiological signals for the patient based on the sequence of depth images, analyzing, using the processor, the sequence of physiological signals for the patient to determine a change in a condition of the patient, and generating a signal to a drug infusion pump in response to determining the change in the condition of the patient.

19 Claims, 11 Drawing Sheets

FALSE ALARM CONTROL AND DRUG TITRATION CONTROL USING NON-CONTACT PATIENT MONITORING

BACKGROUND

Apnea is a common problem affecting premature infants. This apnea of prematurity (AOP) may be due to "physiologic" immaturity of respiratory control that may be exacerbated by neonatal disease. Management of AOP may include using prone positioning and continuous positive or nasal intermittent positive pressure. Drug therapy (i.e. methylxanthine compounds such as caffeine, theophylline, and aminophylline) is a mainstay of treatment of central apnea by stimulating the central nervous system and respiratory muscle function.

A range of depth sensing technologies are available to determine various physiological and contextual parameters, including respiration rate, tidal volume, minute volume, effort to breathe, activity, presence in bed, etc., that may be useful in detecting condition of a patient. However, when a patient is apneic with a central apnea, there may be no physiological motion to indicate that the person is actually present in the scene. Therefore, it may be difficult to distinguish between when a patient has left a bed or when the patient is exhibiting a central apnea.

SUMMARY

Implementations described herein discloses, a method of controlling drug titration to a patient, the method including receiving, using a processor, a sequence of depth images, each depth image including depth information for at least a portion of the patient, determining, using the processor, a sequence of physiological signals for the patient based on the sequence of depth images, analyzing, using the processor, the sequence of physiological signals for the patient to determine a change in a condition of the patient, and generating a signal to a drug infusion pump in response to determining the change in the condition of the patient.

A method of controlling drug titration to a patient disclosed herein includes receiving, using a processor, a sequence of depth images, each depth image comprising depth information for at least a portion of the patient, determining, using the processor, a sequence of physiological signals for the patient based on the sequence of depth images, analyzing, using the processor, the sequence of physiological signals for the patient to determine a change in a condition of the patient and generating a signal to a drug infusion pump in response to determining the change in the condition of the patient. In one implementation, the sequence of physiological signals comprises a sequence of volume signals associated with breathing by the patient. Alternatively, the change in condition of the patient comprises cessation of breathing by the patient.

In an alternative implementation, generating a signal to a drug-infusion pump comprises generating a signal to titrate an anti-apnea drug to the patient. Yet alternatively, generating a signal to a drug infusion pump comprises generating a wait period before the drug-infusion pump initiated titration of an anti-apnea drug to the patient. In another implementation, the method further includes monitoring the volume signals associated with breathing by the patient during the wait period and in response to determining resumption of breathing by the patient, generating a request to the drug-infusion pump to not initiate the drug infusion. In another implementation, generating a signal to a drug infusion pump comprises generating a set time period for the drug-infusion pump to infuse an anti-apnea drug to the patient.

In one implementation, the method further includes generating a vibration signal in response to determining the change in the condition of the patient and communicating the vibration signal to a bed used by the patient. Alternatively, the method further includes generating information about a number of episodes of cessation of breathing by the patient and the average length of the episodes of cessation of breathing by the patient and displaying the information to a clinician. In one implementation, the sequence of depth images comprising depth images before the patient is on a mattress and depth images after the patient is placed on the mattress. In another implementation, the method further includes determining a baseline depth level based on the depth images before the patient is on the mattress, determining a modified depth level based on the depth images after the patient is on the mattress, and calculating a patient envelope volume based on the baseline depth level and the modified depth level. Alternatively, the method further includes comparing the patient envelope volume to a threshold envelope volume to determine that the patient has been removed from the mattress and communicating, in response to determining that the patient has been removed from the mattress, a signal to the drug infusion pump to stop drug-infusion.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

A further understanding of the nature and advantages of the present technology may be realized by reference to the figures, which are described in the remaining portion of the specification.

Figure 8:
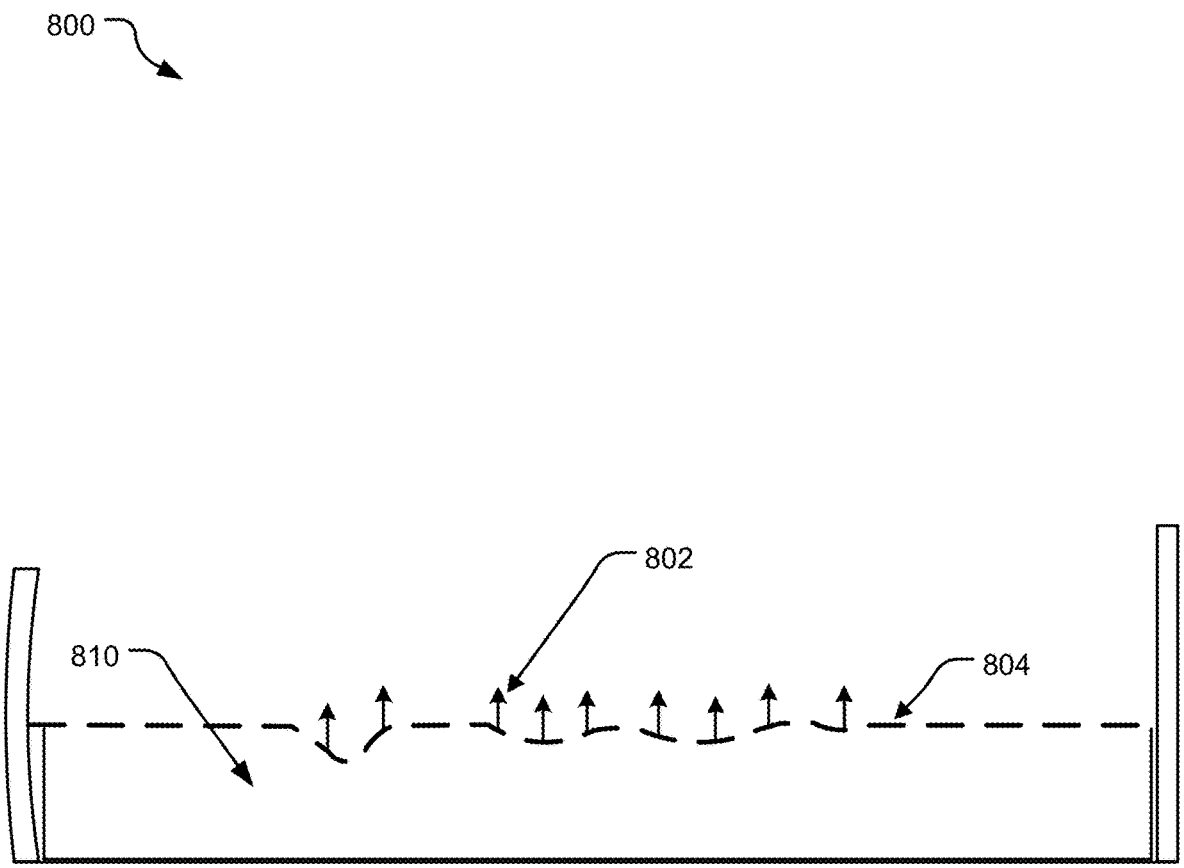

FIG. 8 another modified baseline depth-level when a patient is removed from the mattress.

Figure 9A:
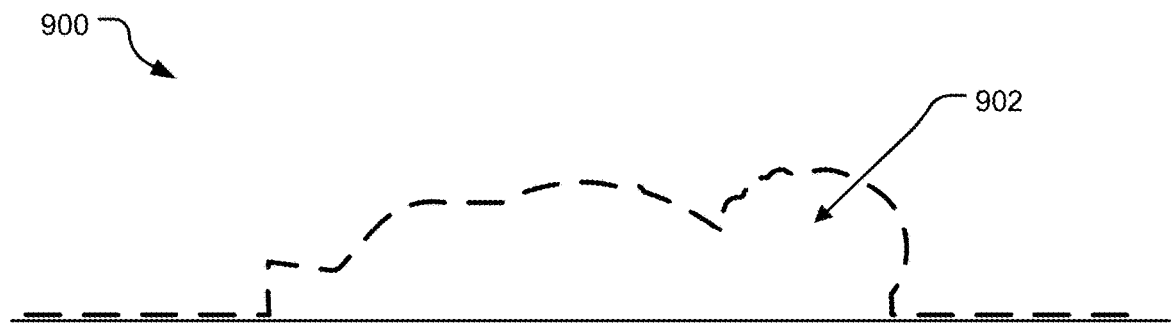
Figure 9B:
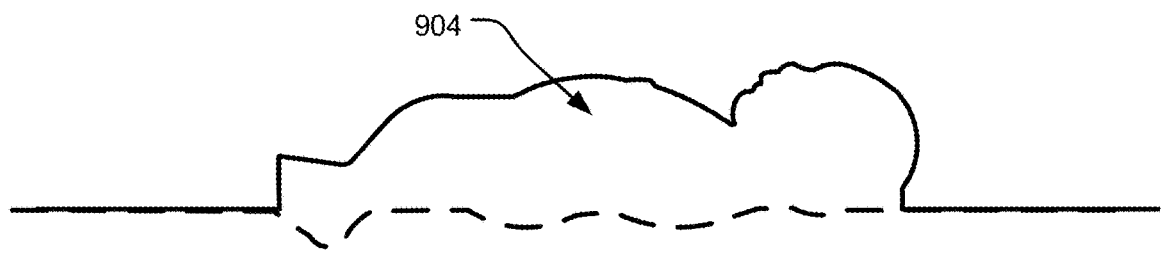
Figure 9C:

FIGS. 9A-9C illustrate various envelopes of depth-level differences that may be determined by analyzing the depth-images from a depth-camera.

Figure 10:
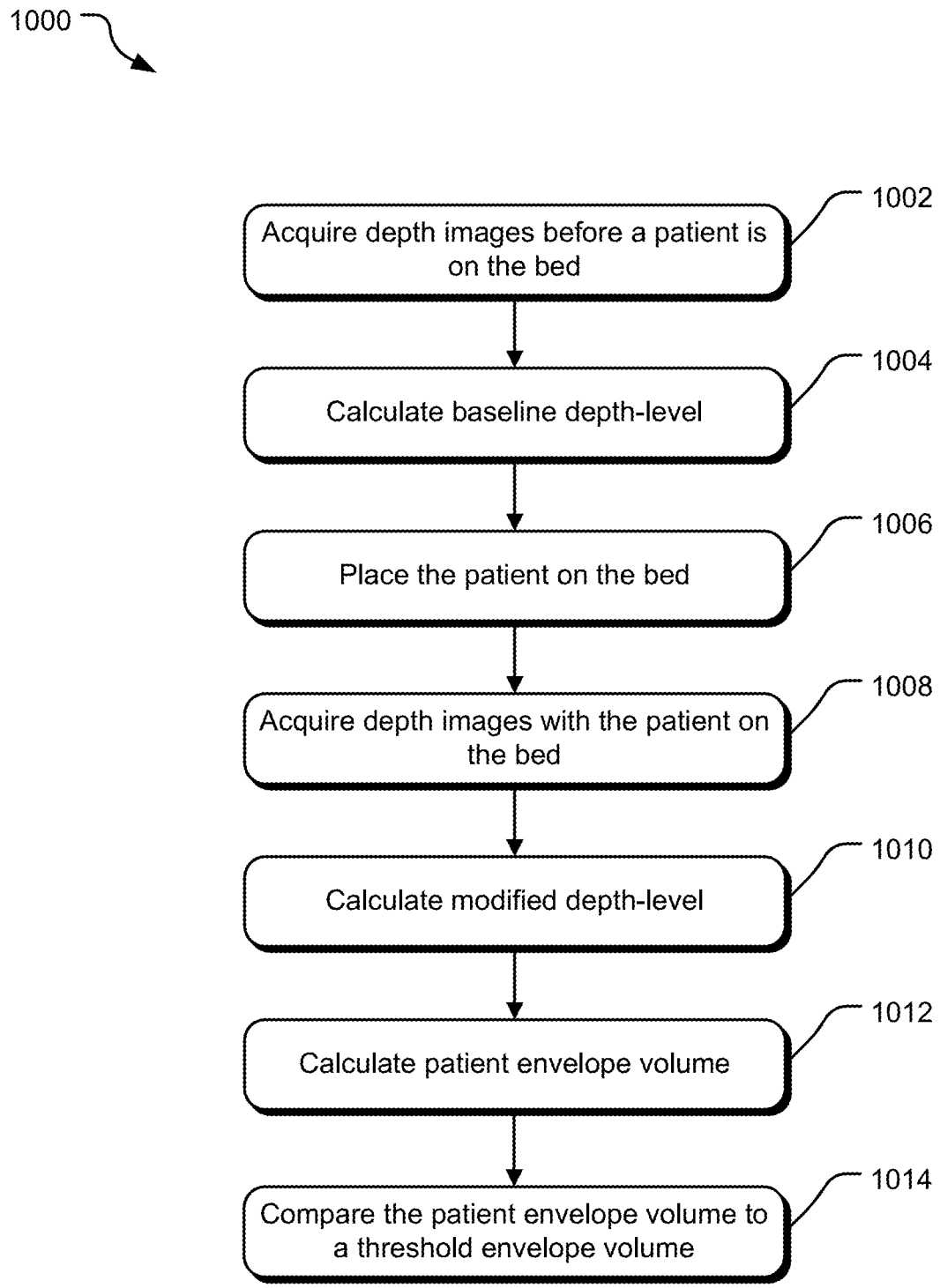

FIG. 10 illustrates an example flowchart with operations for determining if a patient has been removed from bed.

Figure 11:
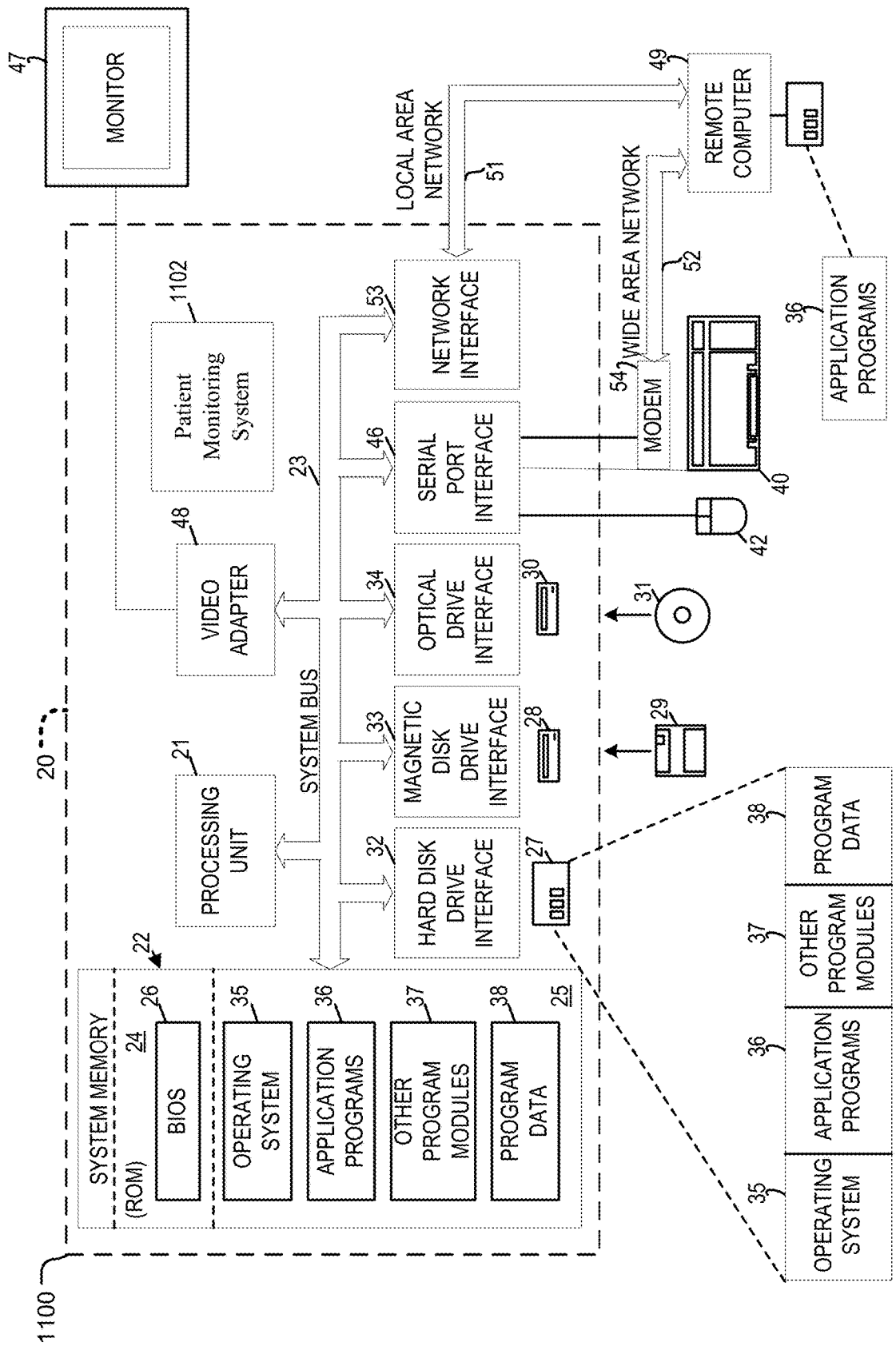

FIG. 11 illustrates an example computing system that may be useful in implementing the described technology.

DETAILED DESCRIPTIONS

Many conventional medical monitors require attachment of a sensor to a patient in order to detect physiologic signals from the patient and transmit detected signals through a cable to the monitor. These monitors process the received signals and determine vital signs such as the patient's pulse rate, respiration rate, and arterial oxygen saturation. For example, a pulse oximeter is a finger sensor that may include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a new field of patient monitoring that uses a remote video camera to detect physical attributes of the patient. This type of monitoring may also be called "non-contact" monitoring in reference to the remote video sensor, which does not contact the patient. The remainder of this disclosure offers solutions and improvements in this new field.

Figure 1:
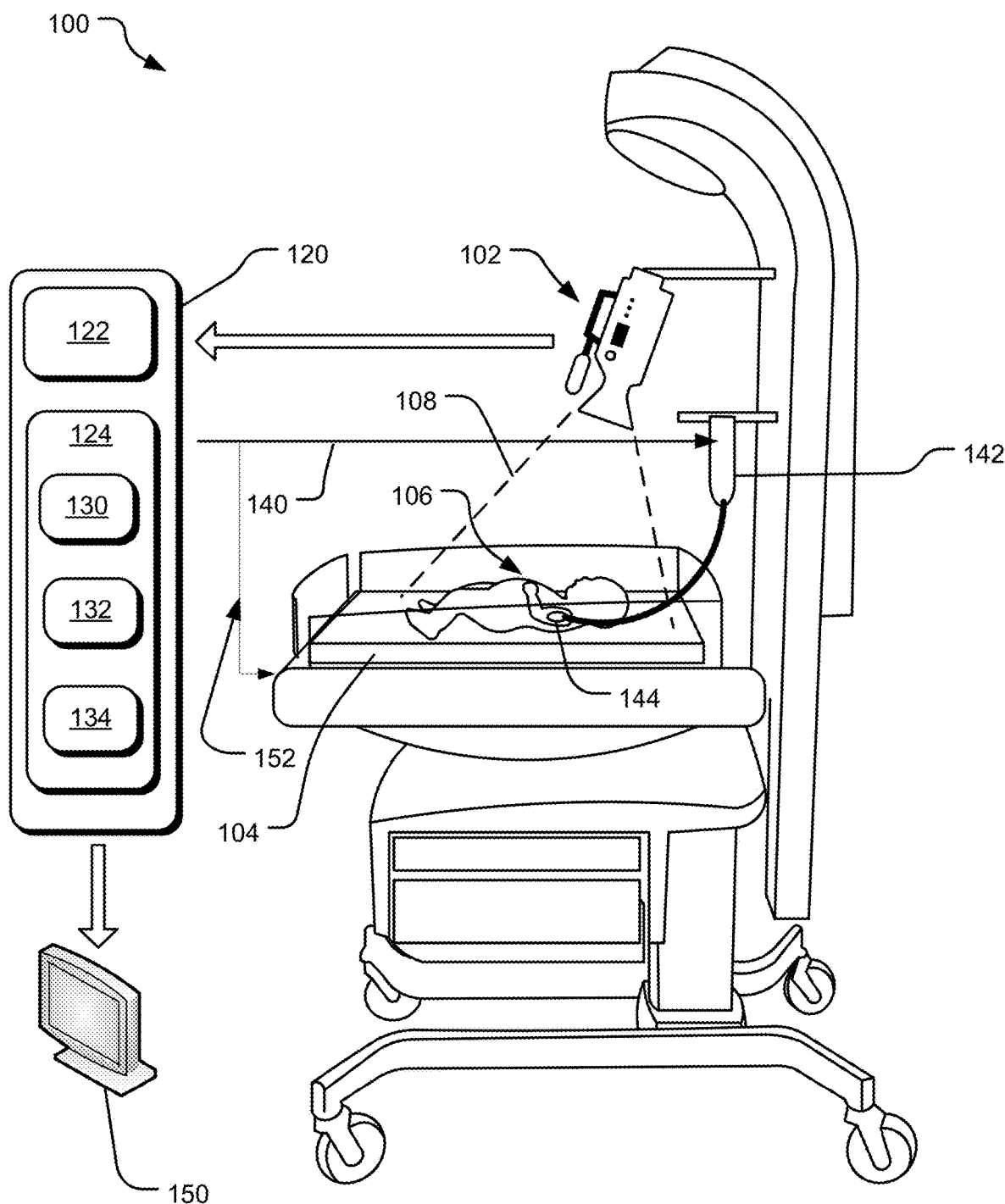
FIG. 1 illustrates an example schematic view of a video based drug titration system for a patient as disclosed herein.

Specifically, a method disclosed herein allows generating a physiological signal using a depth sensing camera system. Such physiological signal may be a volume signal associated with the breathing of a patient. The physiological signal may be analyzed and the output of the analysis may control titration of a drug to the patient. FIG. 1 illustrates a schematic view of such a video based drug titration system 100 for a patient as disclosed herein. The drug titration system 100 includes a camera 102 that monitors a patient 106. For example, the patient 106 may be a neo-natal patient that lying on bed 104 configured on a neo-natal patient caring system. The camera 102 is configured remote from the patient 106, in that it is spaced apart from and does not contact the patient 106. The camera 102 includes a detector exposed to a field of view 108 that encompasses at least a portion of the patient 106 and the bed 104.

The camera 102 may be depth-sensing camera that generates a sequence of images over time. A depth sensing camera can detect a distance between the camera and objects in its field of view and such information can be used to determine that the patient 106 is within the field of view 108 of the camera 102. Note that while FIG. 1 illustrates only one camera 102, in an alternative implementation, multiple cameras 102 may be used to generate multiple sequences of images. Furthermore, while the camera 102 is configured substantially vertically above the patient 106, in alternative implementations, the camera 102, or an additional camera, may be configured substantially on side of the patient 106.

Each of the sequence of images generated by the camera 102 includes the depth information within the field of view 108. The sequence of images generated by the camera 102 are communicated to a computing system 120 that analyzes the sequence of images to generate a series of volume signals associated with the breathing by the patient 106. For example, such volume signals associated with the breathing by the patient 106 may be generated by change in the depth of the chest and/or abdominal regions of the patient 106, as indicated by the sequence of images generated by the camera 102.

The computing system 120 may be a computing system that includes a microprocessor 122, a memory 124, and various other components. An example of such a computing system 120 is disclosed in FIG. 11 below. In a method disclosed herein, the memory 124 may be used to store the sequence of images generated by the camera 102. Furthermore, the memory 124 may also store one or more instructions of an image sequence analysis module 130 that can be executed using the micro-processor 122 to analyze the sequence of images generated by the camera 102 to derive volume signals associated with the breathing by the patient 106.

Furthermore, the memory 124 may also include instructions to analyze the volume signals associated with the breathing by the patient 106 to detect any episodes of cessation in breathing by the patient 106. For example, a cessation detection module 132 including various instructions that are executable on the microprocessor 122 may be analyze the sequence of volume signals associated with the breathing by the patient 106 to confirm that an event indicating cessation of breathing is taking place. Furthermore, the cessation detection module 132 may also determine that such cessation of breathing is taking place as a result of an onset of apnea or subsequent to an onset of apnea. An example pattern indicating such change in breathing pattern in response to an onset of apnea is further discussed below with respect to FIG. 2.

The memory 124 may also include a drug titration determination module 134 including computer program instructions that, in response to determination of an episode of apnea, determines a titration signal 140 to be communicated to a drug-infusion pump 142 that is configured to infuse drug to the patient 106 via a drug delivery patch 144. For example, the titration signal 140 may include information about the dosage of drug that it to be delivered to the patient 106 via the drug-infusion pump 142. In the example, where the cessation detection module 132 determines that the cessation in breathing is a result of an episode of onset of apnea, the drug-infusion pump 142 may infuse an anti-apnea drug to the patient 106. The anti-apnea drug may be delivered for a set time-period after the confirmation of the onset of apnea and the drug titration determination module 134 may determine such set time period based on its analysis of the sequence of volume signals associated with the breathing by the patient 106 over a time period. Alternatively, the infusion of the anti-apnea drug may be triggered only after a prespecified period of apnea after either the onset or the confirmation of apnea as further disclosed below in FIG. 2.

In one implementation, the drug titration determination module 134 may also generate another signal 152 to the bed 104 to vibrate a mattress on which the patient 106 is lying. Yet alternatively, a signal may be generated to a caregiver about the onset of an apnea episode for the patient 106.

The computing device 120 may collect various information about apnea episodes for the patient 106 over time and display such information to a clinician over a monitor 150. Such displayed information may include the number of apnea episodes over a period of five minutes, an hour, several hours, a day, a week, etc., the average length of such apnea episodes, the average dose of drug infusion required to end the apnea episode, etc.

Figure 2:
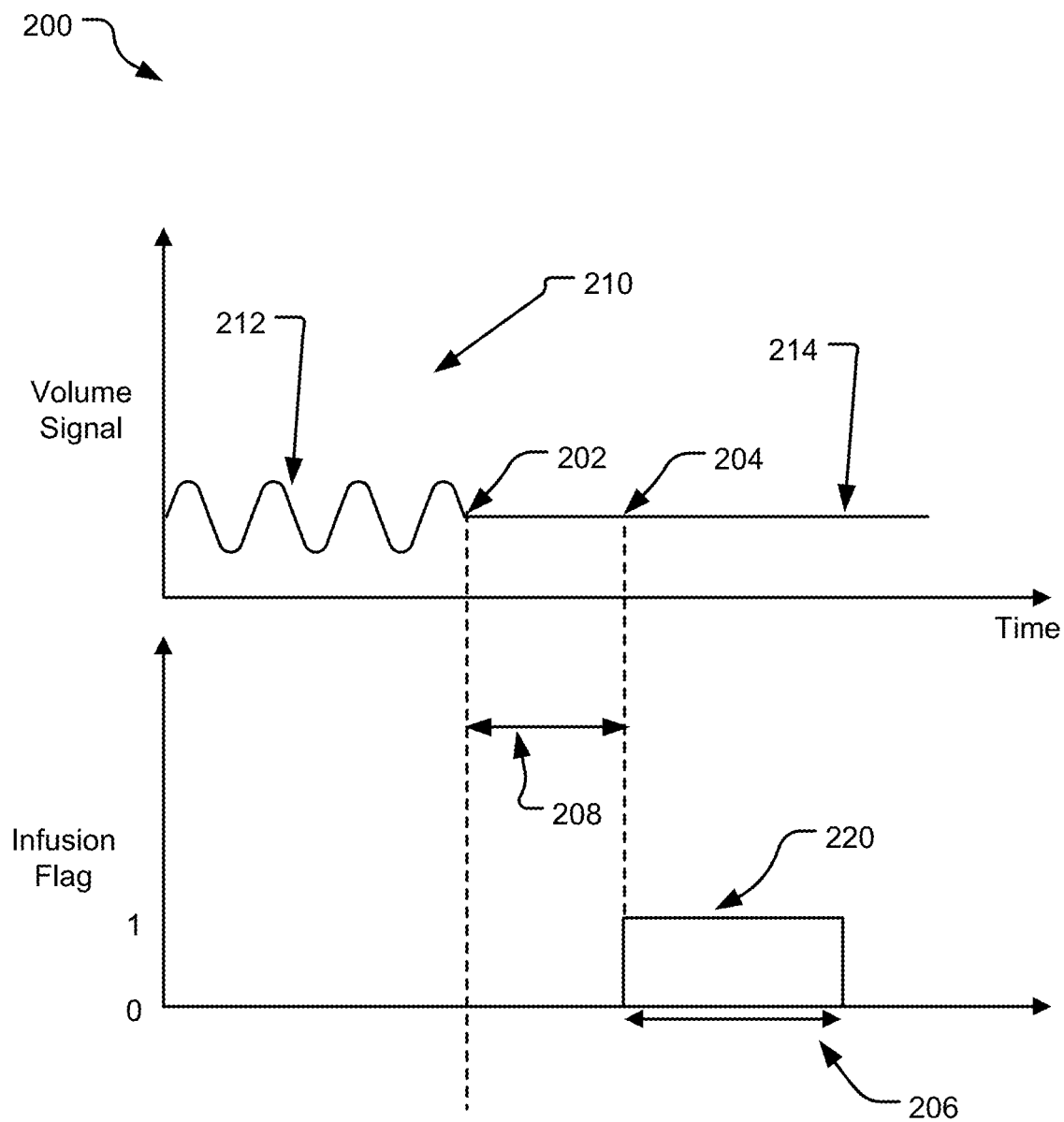
FIG. 2 illustrates example graphs showing a volume signal associated with breathing by a patient and infusion of drug to the patient as disclosed herein.

FIG. 2 illustrates graphs 200 showing a volume signal associated with breathing by a patient and infusion of drug to the patient. Specifically, a graph 210 illustrates the volume signal associated with breathing by a patient indicating detection of cessation of breathing at time 202. As indicated, a volume signal 212 before the time 202 may indicate regular breathing by the patient and a volume signal 214 after the time 202 may indicate lack of breathing. The change of the volume signal from 212 to 214 at time 202 may indicate an episode of onset of apnea.

The drug titration determination module 134 disclosed herein may generate a drug titration signal 220 to a drug-infusion pump after a set time period 208 after the time 202 indicating onset of apnea. The set time period 208 may be determined based on other data related to the patient, such as the number of prior apnea episodes experienced by the patient, the severity of prior apnea episodes experienced by the patient in terms duration, how many apneas were experience by the patient in past hour, day, week, etc., how long were each of such prior apnea episodes, etc. Furthermore, the length 206 of the drug titration signal 220 may also be determined based on other data related to the patient, such as prior apnea episodes experienced by the patient, the severity of the apnea, etc.

Figure 3:
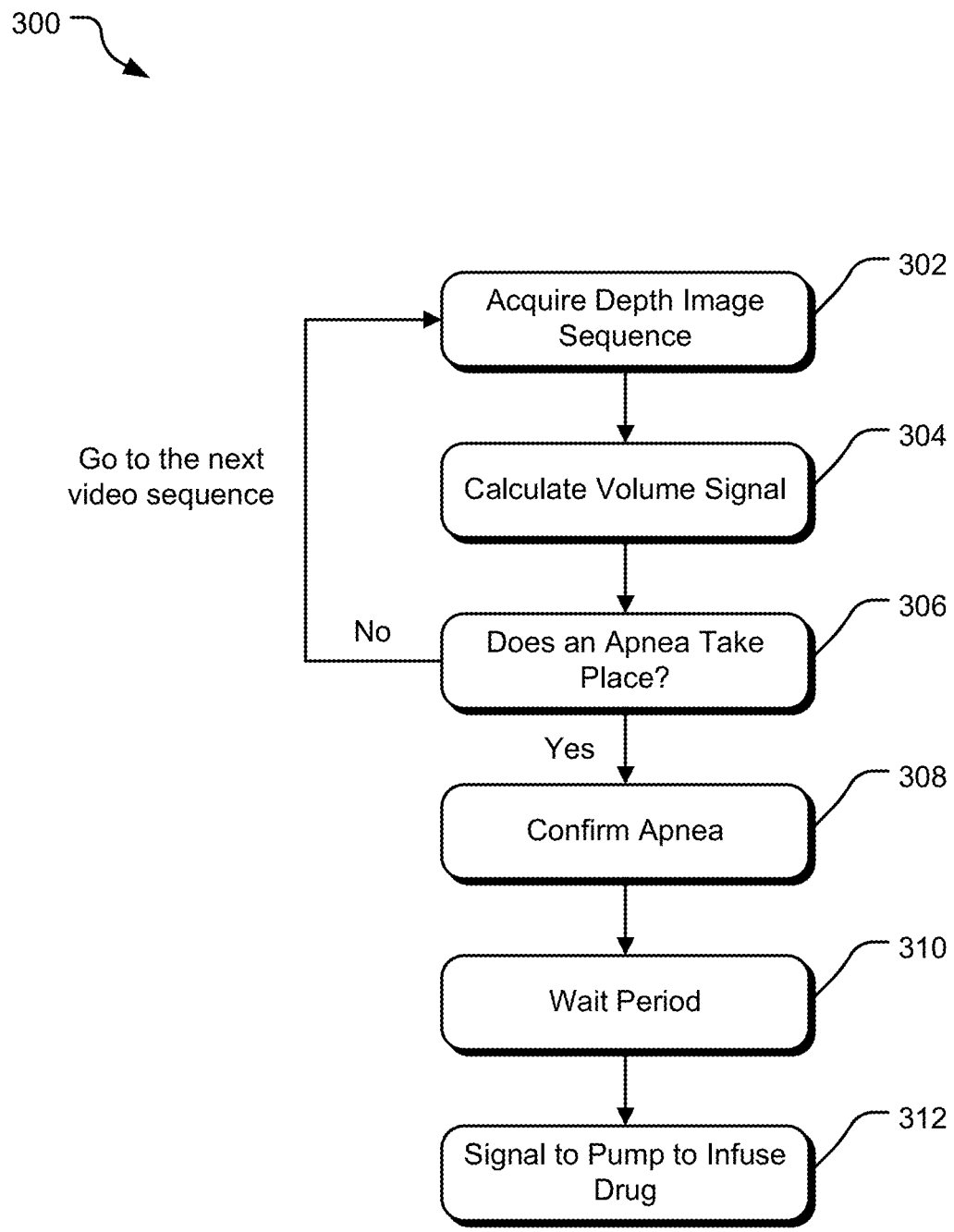
FIG. 3 illustrates an example flowchart with operations for controlling drug-titration to patients based on a sequence of images acquired via non-contact monitoring.

FIG. 3 illustrates a flowchart 300 with operations for controlling drug-titration to patients based on a sequence of images acquired via non-contact monitoring. Specifically, an operation 302 acquires sequence of depth images from a camera. For example, the sequence of depth images may be acquired from a camera above the patient or from multiple cameras arranged around a patient bed. In one implementation, each sequence of depth images may be acquired over a 30 second time-period. An operation 304 may analyze the sequence of depth images to determine calculate volume signals associated with the breathing of the patient. In one implementation, calculating the volume signals associated with the breathing of a patient may include determining a reference point for the patient, determining a region of interest (ROI) based on the reference point, monitoring changes in depth information in the ROI over time, and mapping the monitored changes in the depth information over time to a volume associated with the breathing of a patient.

Subsequently, an operation 306 analyzes the volume signal to determine if an onset of apnea has been detected. If no apnea episode is detected, the next sequence of depth images is acquired to generate a volume signal. If, however, an apnea episode is detected, then operation 308 sets a confirmation flag. An operation 310 triggers a waiting period and at the end of the waiting period, an operation 312 communicates a drug-infusion signal to a drug-infusion pump. The signal communicated by operation 312 may also include a set time period during which the drug is to be delivered to the patient. Such set time period for drug delivery may be determined based on past apnea history of the patient.

In one implementation, the collection of the sequence of depth images and generating volume signals associated with the breathing of a patient continues during the wait period. In such an implementation, if the volume signal may indicate that normal breathing pattern has been resumed, no signal is communicated to the drug-infusion pump at operation 312. In yet another implementation, the total delivery of drug to the patient during a drug delivery to the patient may be monitored over time. Yet alternatively, information about a series of apnea episodes may be collected and presented to a clinician on a screen. Such information may include number of apnea episodes over a period of five minutes, an hour, several hours, a day, a week, etc., the average length of such apnea episodes, the average dose of drug infusion required to end the apnea episode, etc.

Figure 4:
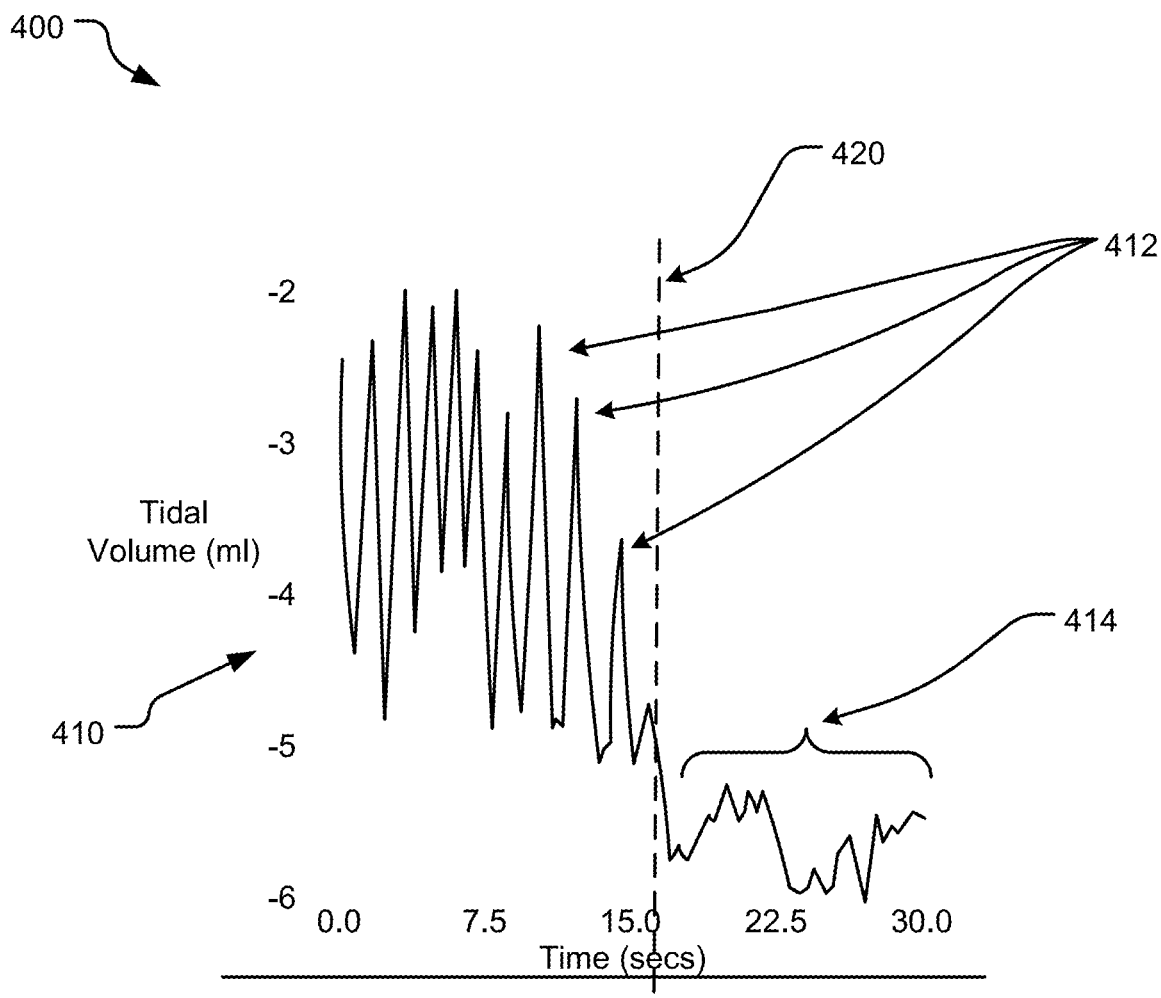
FIG. 4 illustrates a graph of an actual volume signal computed from a sequence of depth images.

FIG. 4 illustrates a graph 400 of an actual volume signal 410 computed from a sequence of depth images. A portion 412 of the volume signal 410 indicates breathing by the patient exhibited by strong regular modulations in the volume signal. An apnea region 414 is indicated by lower and more erratic volume signal modulations. Specifically, the apnea region 414 is not flat, which may be result of other non-breathing motions of the patient. The technology disclosed herein analyzes the volume signal 410 to determine onset of apnea substantially at time 420.

Figure 5:
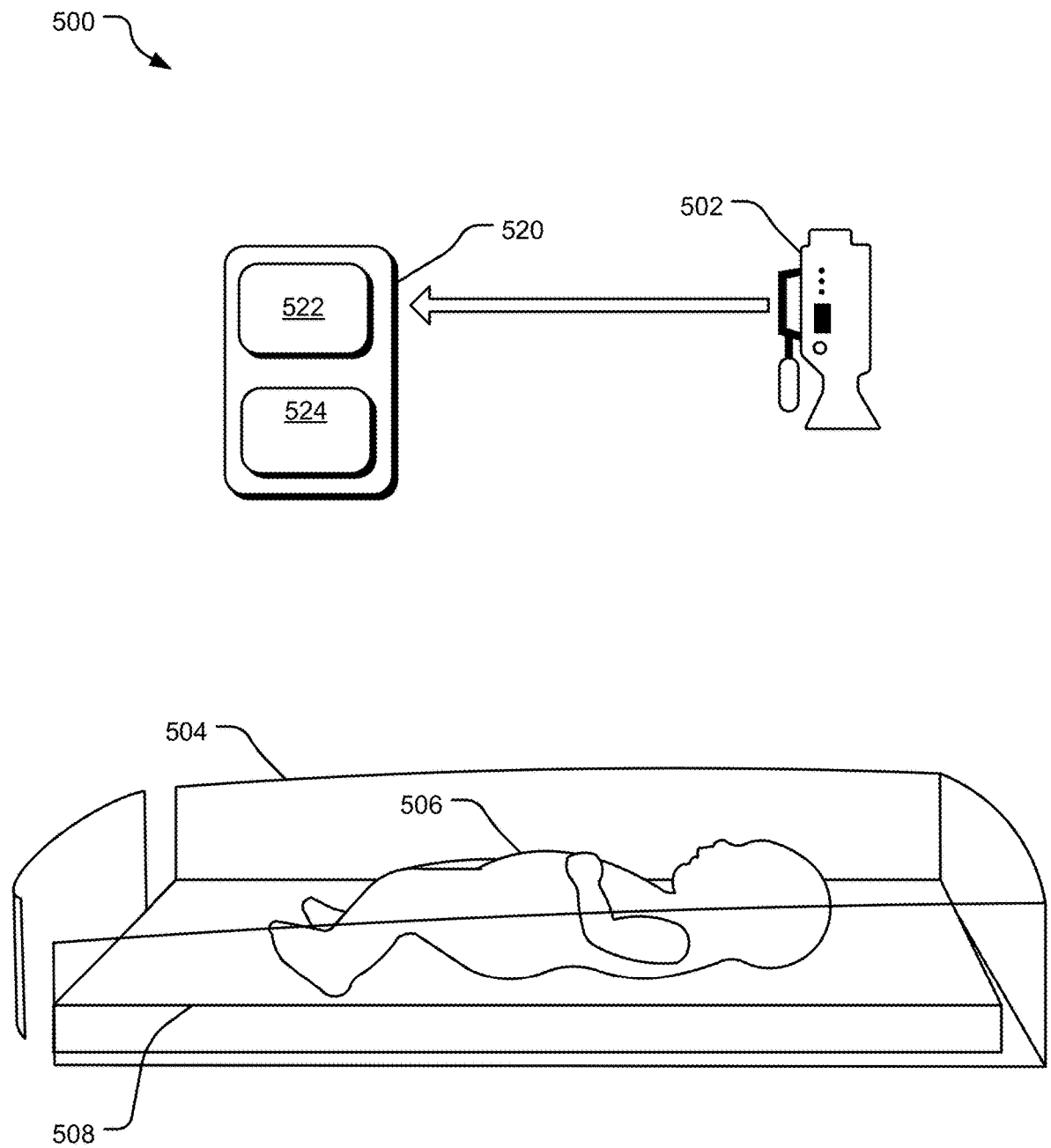
FIG. 5 illustrates an example of a patient in a bed with a depth-camera fixed above the bed 504 to observe the scene.

Furthermore, the technology disclosed herein may also be used to determine, based on determining physiological motion, whether a patient that is apneic with a central apnea is actually present in a bed. This allows avoiding false alarms for apnea when in fact the patient has simply left the bed. Specifically, FIG. 5 illustrates an example of a patient 506 in a bed 504 with a depth-camera 502 fixed above the bed 504 to observe the scene. For example, the patient 506 may be a neonate. The bed 504 may include a mattress 508. Furthermore, while the depth-camera 502 is illustrated to be substantially vertically above the patient 506, in alternative implementations, the depth-camera may be configured to the side of the patient 506.

In a method disclosed herein, before the patient 506 is placed in the bed 504, a baseline levels of depth of the mattress 508 may be determined by analysis of a sequence of depth-images generated by the depth-camera 502. The sequence of depth-images may be communicated to a computing device 520. The computing device 520 may include a microprocessor 522 and a memory 524. Specifically, the memory 524 may store the sequence of depth-images and analyze the sequence of depth-images to generate various levels of depth of the mattress 508.

Figure 6A:
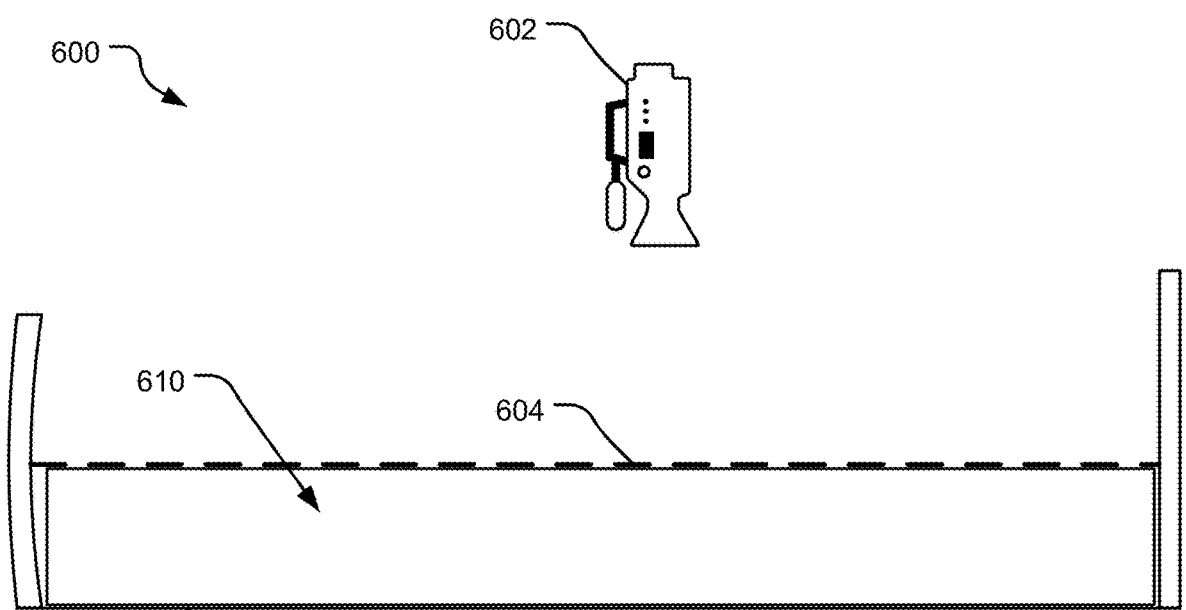
FIG. 6A illustrates a baseline depth-level of a mattress before a patient is placed in a bed.

FIG. 6A illustrates a baseline depth-level 604 of a mattress before a patient 606 is placed in a bed 608. In this illustration, the baseline depth-level 604 is the level of the top of a mattress 610. The baseline depth-level 604 may be determined based on analysis of a sequence of depth-images taken by a depth-camera 602.

Figure 6B:
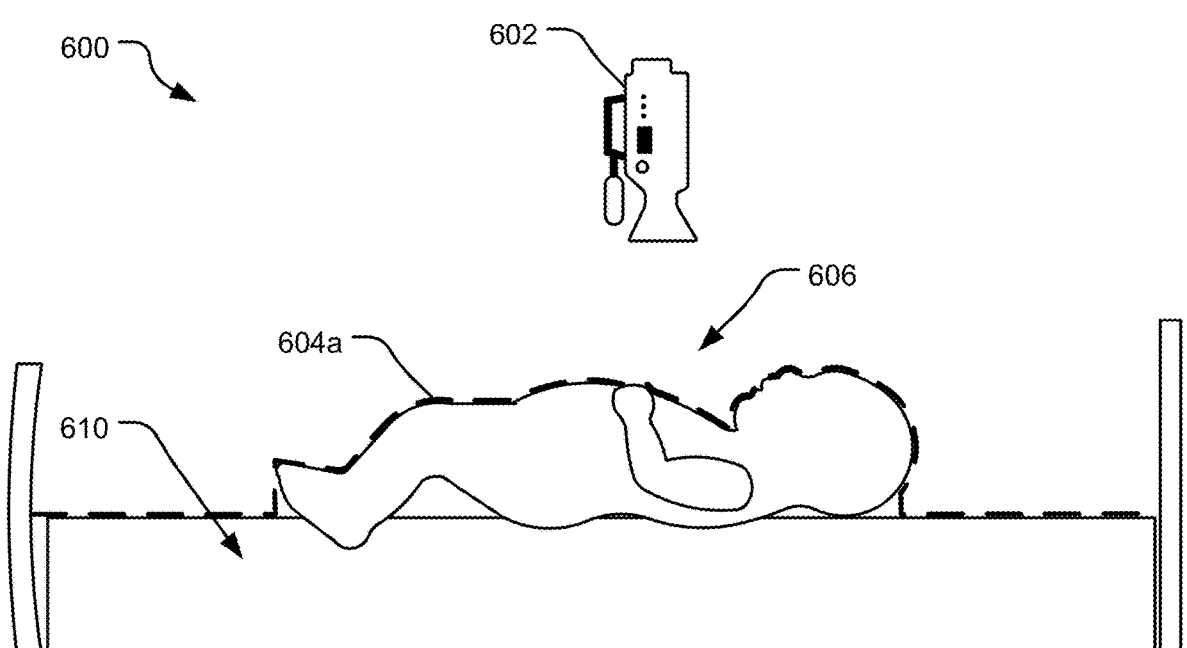
FIG. 6B illustrates an updated depth-level after a patient is placed on the mattress.

FIG. 6B illustrates an updated depth-level 604a after a patient 606 is placed on the mattress 610. As seen the updated depth-level 604a corresponds to morphology of the patient 606 as sensed by the depth-camera 602. Specifically, the updated depth-level 604a differs from the baseline depth-level 604 across the region of interest. The differences between the baseline depth-level 604 and the updated depth-level 604a are calculated using one or more computing instructions stored in a memory of a computing device and then stored in the memory. In one implementation, the differences between the baseline depth-level 604 and the updated depth-level 604a are stored as a series of co-ordinates in a 3-dimensional (3D) space. Alternatively, the differences between the baseline depth-level 604 and the updated depth-level 604a are integrated to determine a volume of the patient 606 above the baseline depth-level 604 of the mattress 610.

Figure 7:
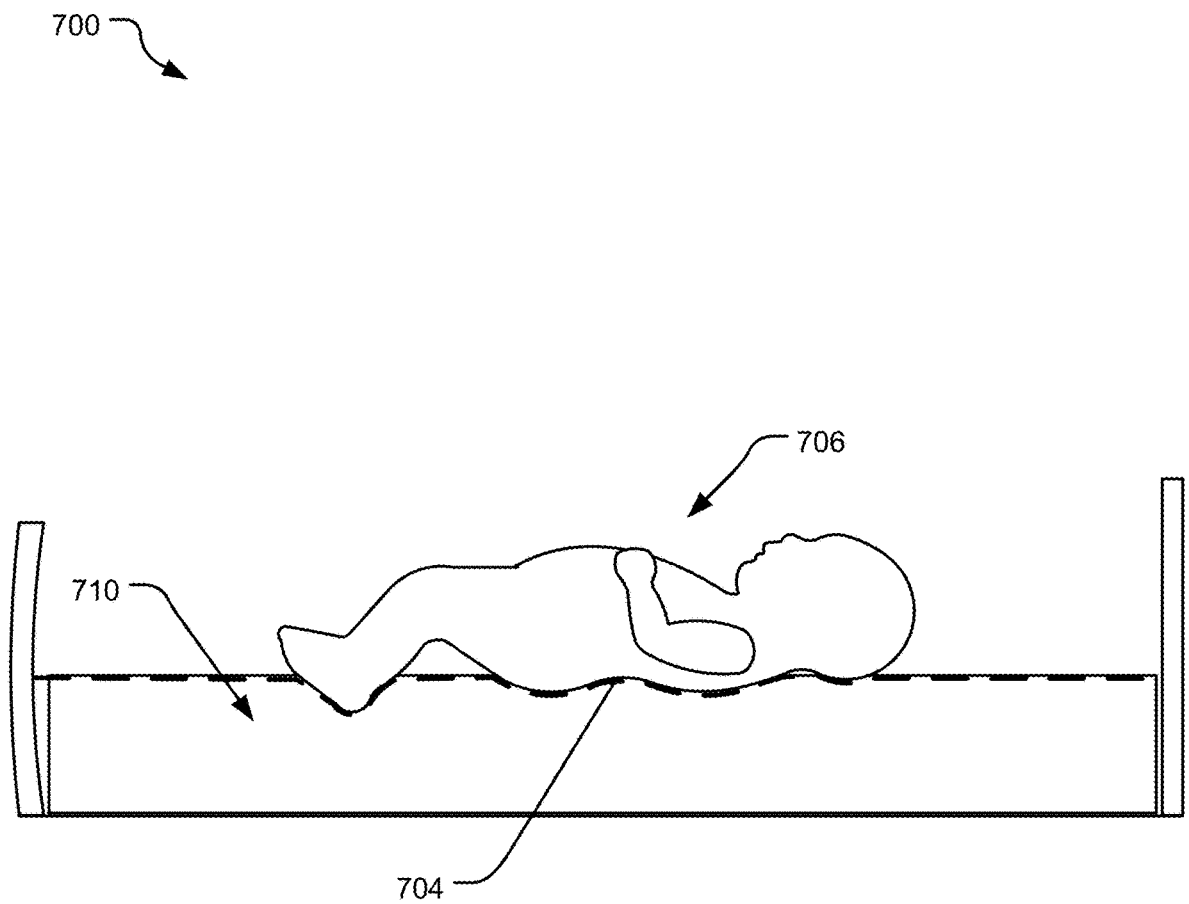
FIG. 7 illustrates a modified baseline depth-level of a mattress as a result of placing a patient on the mattress.

FIG. 7 illustrates a modified baseline depth-level 704 of a mattress 710 as a result of placing a patient 706 on the mattress 710. This is the result of the patient 706 compressing the mattress 710. Specifically, a top level of the mattress 710 becomes deformed and is lower than the baseline depth-level 604.

FIG. 8 illustrates another modified baseline depth-level 804 when a patient is removed from the mattress 810. Specifically, the arrows 802 illustrate how the mattress slowly begins to expand back to its original position as the patient is removed from the mattress 810. As a result, the differences between the compressed modified baseline depth-level 704 and the the baseline depth-level 604 starts to reduce. Various depth-levels 604, 604a, 704, 804, are stored in a memory and tracked over time to detect removal of a patient from a bed.

FIG. 9 illustrates various envelopes of depth-level differences that may be determined by analyzing the depth-images from a depth-camera. Specifically, 902 illustrates an envelope of depth-level difference between a baseline depth-level of a mattress and a depth-level of a patient on the mattress. 904 illustrates an envelope of depth-level difference between a depressed mattress level due to the patient being on the mattress and a depth-level of a patient on the mattress. On the other hand, 906 illustrates an envelope of depth-level difference between the a depressed mattress level due to the patient being on the mattress and the baseline depth-level of a mattress.

Detection of these envelopes may be used to determine presence of a patient on the bed or removal of the patient from the bed. Specifically, when a patient is removed from the bed, a different signal may be generated to a caregiver or a clinician that the patient is absent from bed compared a signal that indicates that the patient has experienced an episode of apnea. In one implementation, before any drug-infusion signal is communicated a drug-infusion pump, the envelope volumes as disclosed in FIG. 9 may be analyzed to ensure that the signal indicating cessation of breathing is not due to the patient being removed from the bed.

FIG. 10 illustrates a flowchart 1000 with operations for determining if a patient has been removed from bed. An operation 1002 takes depth-images of a bed before a patient is placed on the bed. An operation 1004 analyzes these depth-images of a bed to determine a baseline depth-level. Subsequently, at operation 1006, the patient is placed on the bed. An operation 1008 takes depth-images with the patient on the bed. An operation 1010 analyzes these depth-images of a bed to determine a modified depth-level. Using the baseline depth-level and the modified depth-level, an operation 1012 calculates an envelope volume of the patient.

Subsequently, an operation 1014 evaluates the patient envelope volume to a threshold volume level and if the envelope volume is below the threshold, it generates as signal that the patient has been removed from the bed or the mattress.

FIG. 11 illustrates an example system 1100 that may be useful in implementing the described technology for providing attestable and destructible device identity. The example hardware and operating environment of FIG. 11 for implementing the described technology includes a computing device, such as a general-purpose computing device in the form of a computer 20, a mobile telephone, a personal data assistant (PDA), a tablet, smart watch, gaming remote, or other type of computing device. In the implementation of FIG. 11, for example, the computer 20 includes a processing unit 21, a system memory 22, and a system bus 23 that operatively couples various system components including the system memory to the processing unit 21. There may be only one or there may be more than one processing unit 21, such that the processor of the computer 20 comprises a single central-processing unit (CPU), or a plurality of processing units, commonly referred to as a parallel processing environment. The computer 20 may be a conventional computer, a distributed computer, or any other type of computer; the implementations are not so limited.

The system bus 23 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 24 and random-access memory (RAM) 25. A basic input/output system (BIOS) 26, containing the basic routines that help to transfer information between elements within the computer 20, such as during start-up, is stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated tangible computer-readable media provide non-volatile storage of computer-readable instructions, data structures, program modules and other data for the computer 20. It should be appreciated by those skilled in the art that any type of tangible computer-readable media may be used in the example operating environment.

A number of program modules may be stored on the hard disk drive 27, magnetic disk 28, optical disk 30, ROM 24, or RAM 25, including an operating system 35, one or more application programs 36, other program modules 37, and program data 38. A user may generate reminders on the personal computer 20 through input devices such as a keyboard 40 and pointing device 42. Other input devices (not shown) may include a microphone (e.g., for voice input), a camera (e.g., for a natural user interface (NUI)), a joystick, a game pad, a satellite dish, a scanner, or the like. These and other input devices are often connected to the processing unit 21 through a serial port interface 46 that is coupled to the system bus 23, but may be connected by other interfaces, such as a parallel port, game port, or a universal serial bus (USB) (not shown). A monitor 47 or other type of display device is also connected to the system bus 23 via an interface, such as a video adapter 48. In addition to the monitor, computers typically include other peripheral output devices (not shown), such as speakers and printers.

The computer 20 may operate in a networked environment using logical connections to one or more remote computers, such as remote computer 49. These logical connections are achieved by a communication device coupled to or a part of the computer 20; the implementations are not limited to a particular type of communications device. The remote computer 49 may be another computer, a server, a router, a network PC, a client, a peer device or other common network node, and typically includes many or all of the elements described above relative to the computer 20. The logical connections depicted in FIG. 11 include a local-area network (LAN) 51 and a wide-area network (WAN) 52. Such networking environments are commonplace in office networks, enterprise-wide computer networks, intranets and the Internet, which are all types of networks.

When used in a LAN-networking environment, the computer 20 is connected to the local network 51 through a network interface or adapter 53, which is one type of communications device. When used in a WAN-networking environment, the computer 20 typically includes a modem 54, a network adapter, a type of communications device, or any other type of communications device for establishing communications over the wide area network 52. The modem 54, which may be internal or external, is connected to the system bus 23 via the serial port interface 46. In a networked environment, program engines depicted relative to the personal computer 20, or portions thereof, may be stored in the remote memory storage device. It is appreciated that the network connections shown are examples and other means of communications devices for establishing a communications link between the computers may be used.

In an example implementation, software or firmware instructions for providing attestable and destructible device identity may be stored in memory 22 and/or storage devices 29 or 31 and processed by the processing unit 21. One or more datastores disclosed herein may be stored in memory 22 and/or storage devices 29 or 31 as persistent datastores. For example, a patient monitoring system 1102 may be implemented on the computer 20 (alternatively, the patient monitoring system 1102 may be implemented on a server or in a cloud environment). The patient monitoring system 1102 may utilize one of more of the processing unit 21, the memory 22, the system bus 23, and other components of the personal computer 20.

In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A method of controlling drug titration to a patient, comprising:
   receiving, using a processor, a first sequence of depth images, each depth image comprising depth information for at least a portion of a mattress before the patient is placed on the mattress;
   receiving, using the processor, a second sequence of depth images, each depth image comprising depth information for at least a portion of the patient;
   calculating a patient envelope volume based on the first sequence of depth images and the second sequence of depth images;
   determining, using the processor, a sequence of physiological signals for the patient based on the second sequence of depth images;
   analyzing, using the processor, the sequence of physiological signals for the patient to determine a change in a condition of the patient; and
   generating a signal to a drug infusion pump in response to determining the change in the condition of the patient.

2. The method of claim 1, wherein the sequence of physiological signals comprises a sequence of volume signals associated with breathing by the patient.

3. The method of claim 2, wherein the change in condition of the patient comprises cessation of breathing by the patient.

4. The method of claim 3, further comprising generating information about a number of episodes of cessation of breathing by the patient and the average length of the episodes of cessation of breathing by the patient and displaying the information to a clinician.

5. The method of claim 2, wherein generating a signal to a drug-infusion pump comprises generating a signal to titrate an anti-apnea drug to the patient.

6. The method of claim 2, wherein generating a signal to a drug infusion pump comprises generating a wait period before the drug-infusion pump initiated titration of an anti-apnea drug to the patient.

7. The method of claim 6, further comprising monitoring the volume signals associated with breathing by the patient during the wait period and in response to determining resumption of breathing by the patient, generating a request to the drug-infusion pump to not initiate the drug infusion.

8. The method of claim 2, wherein generating a signal to a drug infusion pump comprises generating a set time period for the drug-infusion pump to infuse an anti-apnea drug to the patient.

9. The method of claim 2, further comprising generating a vibration signal in response to determining the change in the condition of the patient and communicating the vibration signal to a bed used by the patient.

10. The method of claim 1, further comprising:
    determining a baseline depth level based on the first sequence of depth images; and
    determining a modified depth level based on the second sequence of depth images.

11. The method of claim 10, further comprising:
    comparing the patient envelope volume to a threshold envelope volume to determine that the patient has been removed from the mattress; and
    communicating, in response to determining that the patient has been removed from the mattress, a signal to the drug infusion pump to stop drug-infusion.

12. In a computing environment, a method performed at least in part on at least one processor, the method comprising:
    receiving a sequence of depth images, each depth image comprising depth information for at least a portion of a patient, depth images before the patient is on a mattress, and depth images after the patient is placed on the mattress;
    determining a baseline depth level based on the depth images before the patient is on the mattress;

determining a modified depth level based on the depth images after the patient is on the mattress; and calculating a patient envelope volume based on the baseline depth level and the modified depth level.

13. The method of claim 12, further comprising calculating a difference between the baseline depth level and the modified depth level as a series of coordinates in three-dimensional (3D) space.

14. The method of claim 12, further comprising:

comparing the patient envelope volume to a threshold envelope volume to determine that the patient has been removed from the mattress; and communicating, in response to determining that the patient has been removed from the mattress, a signal to the drug infusion pump to stop drug-infusion.

15. The method of claim 12, further comprising:

determining a sequence of volume signals associated with breathing for the patient based on the sequence of depth images;

analyzing the sequence of volume signals for the patient to determine a change in a condition of the patient; and generating a signal to a drug infusion pump in response to determining the change in the condition of the patient.

16. The method of claim 15, wherein the change in condition of the patient comprises cessation of breathing by the patient.

17. The method of claim 15, wherein generating a signal to a drug-infusion pump further comprising:

generating a signal to a drug-infusion pump comprises generating a signal to titrate an anti-apnea drug to the patient; and generating a wait period before the drug-infusion pump initiated titration of an anti-apnea drug to the patient.

18. A physical article of manufacture including one or more tangible computer-readable storage media, encoding computer-executable instructions for executing on a computer system a computer process to provide an automated connection to a collaboration event for a computing device, the computer process comprising:

receiving a sequence of depth images, each depth image comprising depth information for at least a portion of the patient, depth images before the patient is on a mattress, and depth images after the patient is placed on the mattress;

calculating a patient envelope volume based on the depth images before the patient is on a mattress and depth images after the patient is placed on the mattress;

determining a sequence of volume signals associated with breathing of the patient based on the sequence of depth images;

analyzing the sequence of volume signals associated with breathing of the patient to determine an onset of apnea episode for the patient; and generating a signal to a drug infusion pump in response to determining the change in the condition of the patient.

19. The physical article of manufacture of claim 18, wherein the computer process further comprises generating a wait period before the drug-infusion pump initiated titration of an anti-apnea drug to the patient and monitoring the volume signals associated with breathing by the patient during the wait period and in response to determining resumption of breathing by the patient, generating a request to the drug-infusion pump to not initiate the drug infusion.

* * * * *